United States Patent [19]
Paschal

[11] Patent Number: 4,967,320
[45] Date of Patent: Oct. 30, 1990

[54] DENTAL PROTECTIVE AIR BARRIER LIGHT APPARATUS AND METHOD

[75] Inventor: Richard C. Paschal, Nashville, Tenn.

[73] Assignee: Distinctively Different, Inc., Nashville, Tenn.

[21] Appl. No.: 347,727

[22] Filed: Apr. 24, 1989

[51] Int. Cl.⁵ .................................................. A61C 5/14
[52] U.S. Cl. .......................................... 362/96; 98/36; 433/136; 433/229
[58] Field of Search .............. 362/96; 98/36; 433/136, 433/229

[56] References Cited

U.S. PATENT DOCUMENTS

| | | | |
|---|---|---|---|
| 3,107,863 | 10/1963 | Potapenko | 362/96 |
| 3,806,720 | 4/1974 | Hortig | 362/253 |
| 3,923,482 | 12/1975 | Knab et al. | 98/36 X |
| 4,742,764 | 5/1988 | Duvlis | 98/36 |

FOREIGN PATENT DOCUMENTS 1617977  4/1971  Fed. Rep. of Germany .......... 98/36

Primary Examiner—Allen M. Ostrager

[57] ABSTRACT

An air emitting light and shielding apparatus for dental treatment comprised of a pressurized air source connected to an adjustably positionable air emitting light formed so as to develop an air envelope substantially surrounding the face and oral cavity or other body parts of a patient residing in a selected position in the dental chair or other operating table including positions in which the patient may be tilted such that vapors, blood, saliva splash, dental particles, or other foreign matter propelled from the patient's oral cavity during drilling, air-water syringing, or the like, are deflected by the inner boundary of the air envelope and are transported downstream of the patient's oral cavity for collection on a disposable patient drape thereby preventing the same from reaching the face and respiratory tract of a dental team member operating on the patient. The apparatus may also be used in related medical applications, such as in conjunction with an operating table where the patient may move or be moved about the table surface.

3 Claims, 3 Drawing Sheets

DENTAL PROTECTIVE AIR BARRIER LIGHT APPARATUS AND METHOD

BACKGROUND OF THE INVENTION

1. Field of the Invention

The present invention relates broadly to apparatus and methods utilizing an air barrier emitting light for body protection and more specifically as applied to dentistry for body protection of a dental or other medical team. a dental team normally comprises a dentist, dental assistant, and hygenist.

2. Description of Related Art

A long-standing problem associated with dentistry has been the exposure of the dental team to relatively high velocity amalgram particles, blood aerosols, saliva splash, and the like, generated during drilling, polishing, syringing and like dental operations. Such procedures may extend over a relatively long period of time. The patient may be in a prone or upright position in the dental chair and the patient's head may be tilted to the right or left during treatment or may be erect. Modern dental drills eject a water spray or mist as a coolant which becomes mixed with other foreign matter much of which is propelled or blown from the oral cavity towards the dental team. It is known that such foreign matter may travel as much as thirty inches from the oral cavity and the direction of travel changes when the patient's head is tilted to one side or the other during treatment. Such exposure has long been known to pose a health threat to the dental team because of exposure to patients who have a common cold, influenza, or hepatitis and whose treatment may generate and cause aerosols with pathogens and viral particles to be propelled from the oral cavity. The emission of such foreign matter also exposes the patient and the dental team to possible damage to the eye during treatment. The dental team frequently leave the office with a gravity covering on skin and hair which is not only uncomfortable but is at times offensive with regard to odor emission and may be a source of infection. in offices where nitrous oxide is utilized, the dental team is exposed to nitrous oxide spillage around the patient's mask and mouth during administration of the gas. To date there has been no solution to preventing such contamination.

With the relatively recent spread of AIDS (Acquired Immune Deficiency Syndrome) the dental team is now concerned with an even more serious problem, namely, that of treating the AIDS patient. Recent disclosure by the Centers for Disease Control and reports at the Third International AIDS Conference in Washington, D.C., in Jun., 1987, include a reported case of an apparent transmission of AIDS via infected saliva contact with a cut on a dentist's finger.

The dental professional works in an environment in which numerous pathogens, both blood-borne and saliva-borne can be present. Transmission of hepatitis B, herpes simplex, the common cold and other infectious diseases have been documented are a clear danger in the dental practice. Aerosol produced by high speed air drills with water spray and air-water syringes produce the described air-borne carriers. As a result, various infectious diseases may be transmitted from the patient to the dental team. At the same time, the patient is subject to contamination by saliva spray during conversation with a dental team member. Some protection is afforded by the practice of members of the dental team wearing masks, gloves and gowns during the entire treatment procedure.

While applicant is aware of little scientific evidence at this date to support the contraction of AIDS by means of saliva and blood splash and/or aerosol, more evidence may eventually appear. Regardless of whether more scientific data emerges to prove or disprove an AIDS threat through the contamination of skin and respiratory tract during dental procedures, there is an immediate need among practicing dentists, hygienists, dental assistants and other medical personnel to be shielded from such contamination.

Thus, what is needed is a protective apparatus and method which substantially eliminates or at least reduces and minimizes the described contamination of the dental team or other medical team. It is also desirable that such protective apparatus and method be in a form which leaves the dental team free to perform dental operations of the kind which produce the undesired emissions with minimum interference to vision and minimum interference to hand operations in the area of the mouth of the patient upon which a dental operation is being performed. Of particular importance is that such protective apparatus and method maintain the protection when the patient's head is tilted during treatment and is normally necessary.

Also, it will be understood the same protective apparatus could be used in similar medical environments, such as an operating tables, where blood and other emissions from the patient positioned on the table could prove a danger to the medical team working on the patient.

Since one advantage obtained from the dental light is based upon establishing a specially formed protective air screen envelope surrounding the patient's head and established between the oral cavity and the dental team, mention is made of prior art apparatus utilizing protective air streams. U.S. Pat. Nos. 428,592; 1,646,103; 2,032,101; 2,560,215 and 3,881,478 represent prior art devices having head mounting structure and means mounted on such structure for creating an air stream to prevent externally produced foreign matter from reaching the face of the wearer. Air streams have also been used for ventilation or cooling. Head mounted ventilating devices are described in U.S. Pat. Nos. 735,959; 2,051,730 and 4,282,869. Barber and beautician's chairs equipped with means to force air over the customer's face are found in U.S. Pat. Nos. 2,051,730; 2,420,251 and 3,248,146. U.S. Pat. Nos. 374,424; 2,703,134 and 3,131,967 describe chairs with means for directing an air stream to cool the body of the occupant of the chair.

What can be surmised from the foregoing prior art is that an air stream on head mounted apparatus has been employed to prevent foreign matter propelled toward the face and generated by a source external of the body, e.g., a grinding wheel as in U.S. Pat. No. 428,592 or a source of noxious fumes as in U.S. Pat. No. 1,646,103, from reaching the face. However, the recited prior art did not recognize that an air stream from a source not mounted on the body can be employed as a shield and deflector to prevent moving drill particles, blood, saliva splash, aerosols, and the like, generated within the oral cavity of a patient and propelled outwardly from the mouth of the patient from reaching the face of a dental team member who typically operates near the face of the patient from which such foreign matter is ejected.

U.S. Pat. No. 3,537,447 followed substantially all the recited prior art and taught the concept of mounting on a dental chair an outlet header connected to a blower and an to a blower and an opposed inlet structure connected to a suction source, both of which are required to be positioned substantially directly over the oral cavity in order to function. The '447 patent apparatus teaches the forming of a planar-laminar air stream and refers to use of such stream to reduce the transfer of microorganisms. The '447 apparatus, however, does not create an air stream which envelopes the patient's head and oral cavity and has to be adjusted whenever the patient's head is tilted or otherwise changed in position. Further, the planar-laminar stream once positioned provides only limited protection against particles, blood aerosols, saliva splash, and the like, emanating from the oral cavity in a specific direction. So far as applicant is aware, the '447 patent apparatus has never been marketed in the apparent twenty years of its existence and is not currently available.

Thus, the primary object of the invention becomes that of providing an apparatus and method directed to preventing or at least substantially eliminating exposure of a dental or medical team to foreign matter propelled from the patient, such as from the patient's mouth, during a dental or medical operation. A more specific object is that of providing an apparatus and method utilizing a light emitting an air envelope surrounding the patient's head or other body part, as a means for both confining and collecting hazardous foreign matter propelled in various directions from the patient during a dental operation. Other objects will become apparent as the description proceeds.

SUMMARY OF THE INVENTION

In the illustrated first embodiment, a source of compressed air, either already existing for other purposes, such as a general purpose air compressor, or established for the purpose of the invention, such as a blower, is operatively associated with or incorporated as part of a dental light. A specially designed and adjustably positioned light is connected to the source of compressed air which may be arranged to serve one or more chairs. The light and its surrounding adjustable conduit are mounted off the patient's head so as not to interfere with normal movement or vision of the dental team or to be perceived by the patient as undesirable. The patient may be in a selected prone or upright position. The light and its supporting adjustable conduit may extend from a ceiling housing, a rear cabinet, a dental unit, a wall or floor mount.

The light directs a continuously formed stream or envelope of air surrounding the patient's head during a dental operation. The air envelope can be well defined by nozzle design with generally smooth and flat inner and outer surfaces. During dental procedures such as drilling, reaming, polishing, syringing, and the like, productive of foreign matter propelled from the mouth of the patient, the dental team operates in a normal manner through the transparent air barrier. The air barrier tends to deflect loose particles, blood, saliva, splash, and aerosols generated and propelled from the oral cavity during the dental operation and also to move such loose particles and other foreign matter in a relatively defined direction such that the foreign matter can be made to collect or condense on an extended absorbent drape or other collecting means draped over the patient below the operative site and which effectively serves as a base for the air enclosure or envelope established by the light. The result is that the dental team is substantially protected from such foreign matter and from transmission of infectious disease from the patient without harm or inconvenience to the patient or disruption of normal dental procedures, particularly when the patient's head is tilted during treatment. Furthermore, members of the dental team are no longer contaminated with such grime at the end of the workday.

BRIEF DESCRIPTION OF THE DRAWINGS

FIG. 2 illustrates diagrammatically the variable positions of the air barrier light.

BEST MODE FOR CARRYING OUT THE INVENTION

Figure 1:
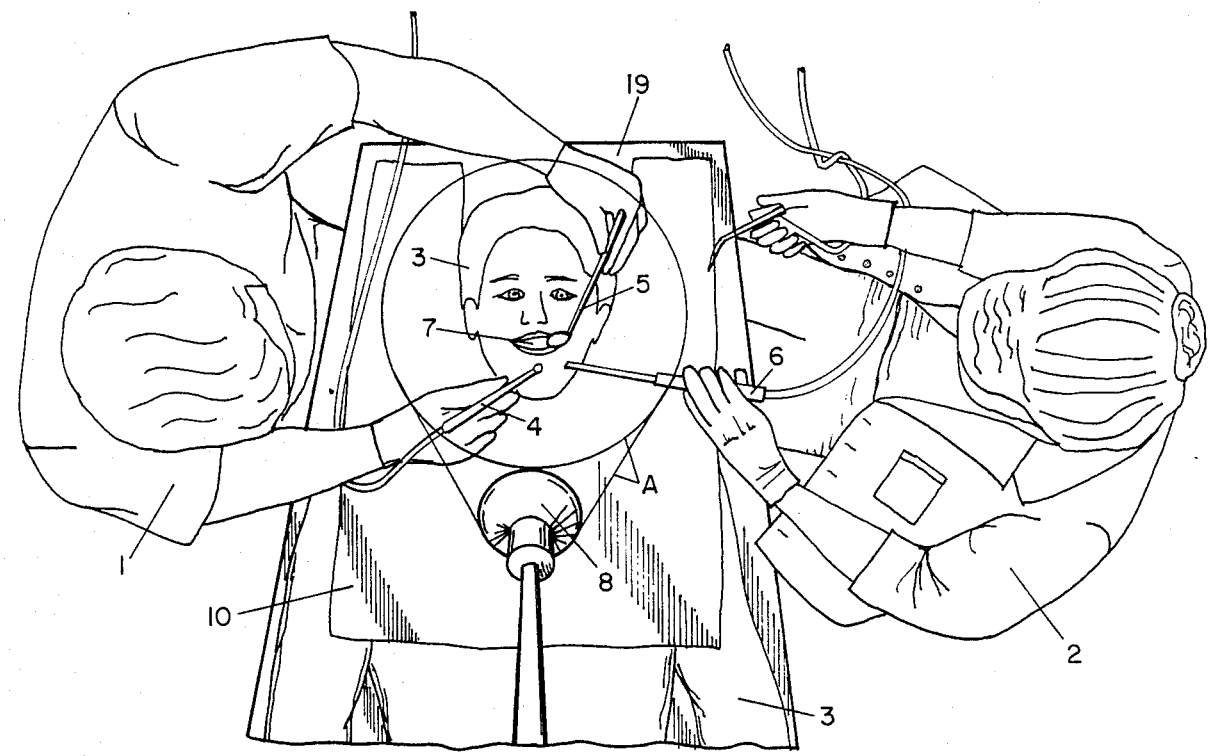
FIG. 1 is a plan view of an operative dental site equipped according to the invention and illustrating in lines A the approximate air flow pattern.

Making reference initially to FIG. 1 of the drawings, there is illustrated a typical dental operative site modified according to the invention. The dentist or hygienist 1, dental assistant 2, and patient 3 are illustrated in a typical dental scene in which the dentist 1 is operating on the patient 3 with an air-operated and water-cooled drill 4 in one hand and a dental tool, e.g., a mirror 5, in the other hand. The dental assistant 2 is illustrated as holding a suction tube 6. What is to be particularly appreciated here is that water and air ejected by drill 4 becomes mixed with saliva and blood from the oral cavity 7 of the patient 3. This air-water-saliva-blood mix along with loose particles from the drilling operation and which may contain aerosols with pathogens as well as viral particles are propelled outwardly from the oral cavity 7 of the patient. Thus, both the dentist or hygienist 1 who are often fourteen to sixteen inches or less from the oral cavity 7 as well as the dental assistant 2 are typically exposed such flying particles, saliva splash, blood aerosols, and the like. Such particles, splash, aerosols, and the like, go in many directions. Some may be propelled as far as thirty inches from the face. Further, the extent of exposure changes when the pateint's head is tilted. Such grime must be periodically removed from the dental team's glasses, faces and frontal head areas and is often extremely difficult to remove and may leave offensive odors in the hair and on the faces of members of the dental team. This most undesirable aspect of dentistry has long existed with no solution and is potentially hazardous with the presence of AIDS and other infectious diseases.

Figure 2:
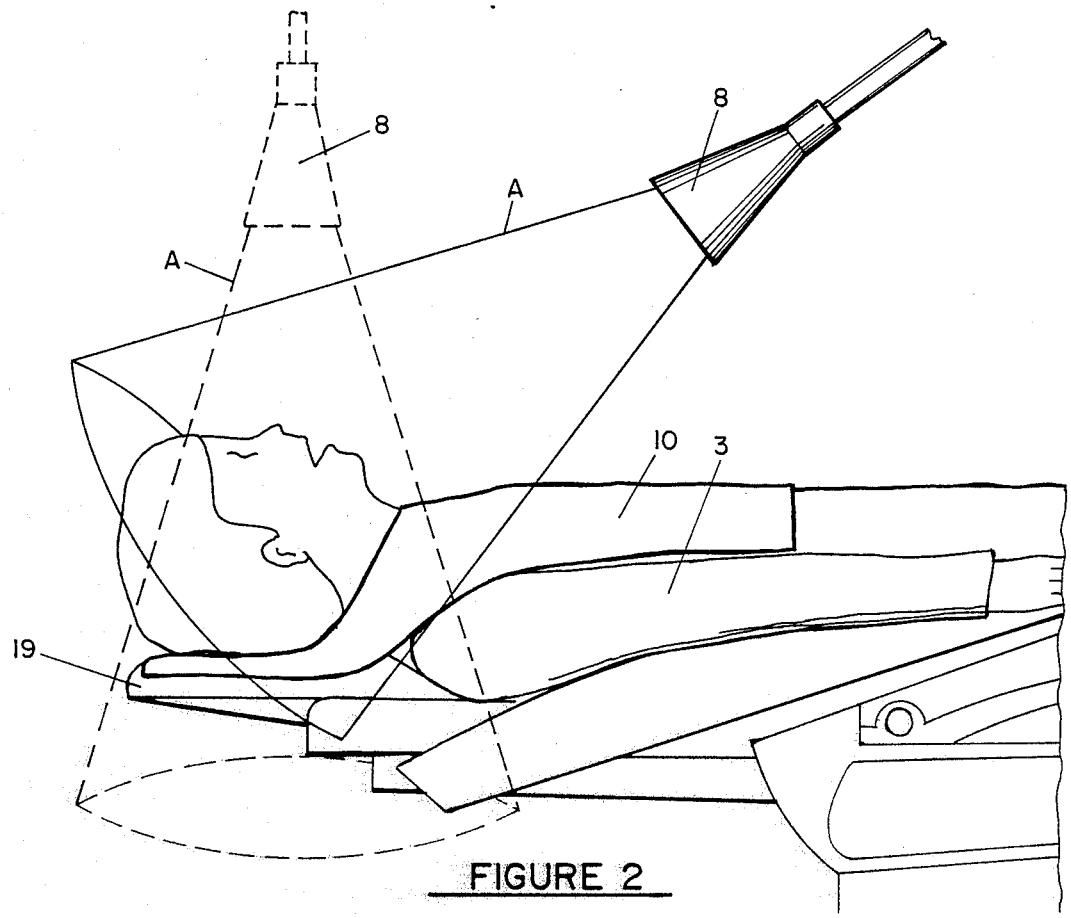
FIG. 2 is a side view of the operative dental site of FIG. 1 diagrammatically illustrating the approximate boundaries of the air flow according to a first embodiment, with foreign matter being confined within the air enclosure and impacting on an absorbent drape 10.

The invention apparatus and method according to a first embodiment illustrated in FIGS. 1 and 2 provides an air emitting light 8 supported above the head of the patient 3. Air Light 8 is connected to a suitable source of compressed air which may comprise a suitably powered air compressor air which may comprise a suitably powered air compressor or conceivably a blower incorporated within the light apparatus. Air Light 8 in this first embodiment mounts on an adjustable light support arms so that it can be appropriately positioned to place the air light 8 in the most desirable position for the particular patient.

Figure 4:
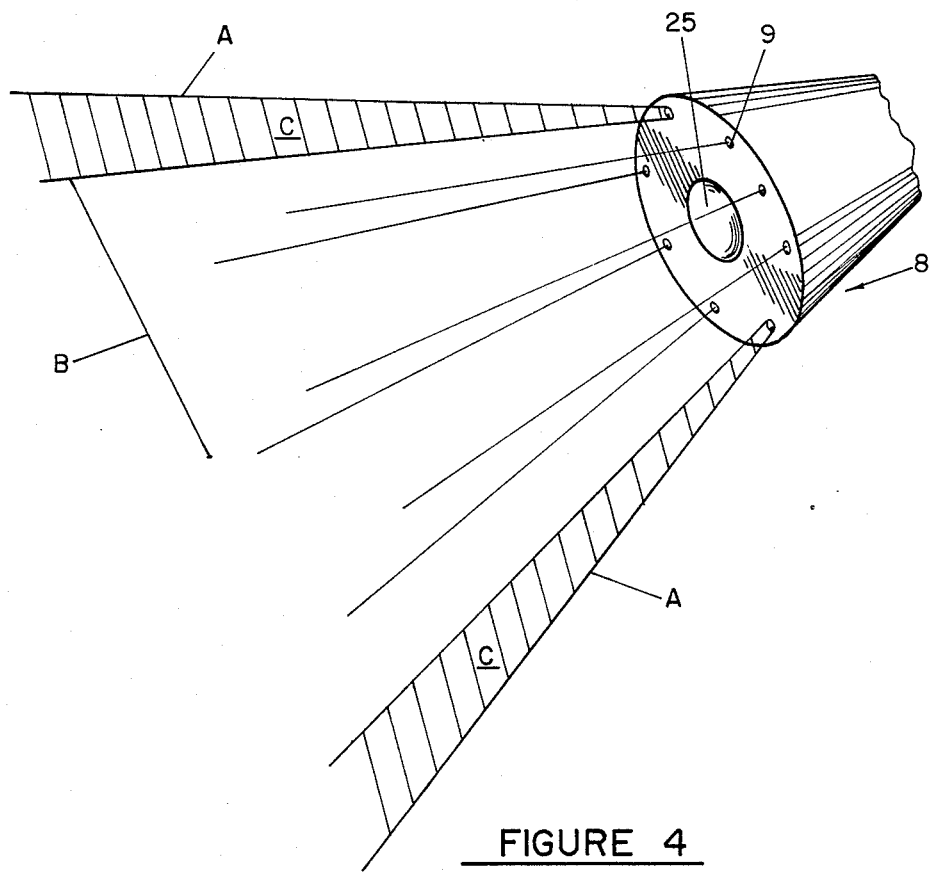
FIG. 4 is a somewhat schematic view of the light illustrated in the embodiment of FIG. 2. Here the light is designed to emit an air envelope from an arrangement of peripheral orifices 9 which surround the light source 8.
Figure 5:
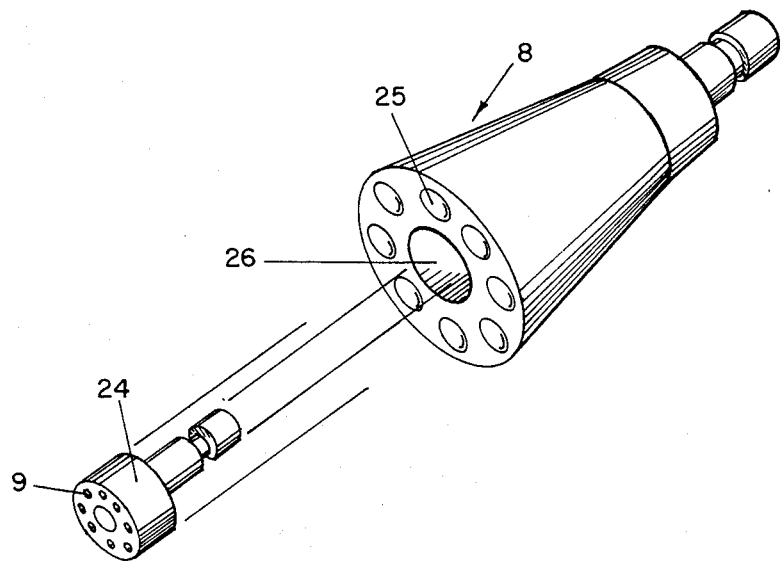
FIG. 5 is a somewhat schematic view of the light illustrated in the embodiment of FIG. 3 with the air envelope originating from a detachable nozzle 24 in the center of light 8 with light source 25 surrounding nozzle socket 26. Here a quick disconnect nozzle is depicted allowing selection of air envelope morphology to meet particular needs to the dental procedure being done.

Air light 8 is equipped internally with orifices 9 arranged diagrammatically illustrated in FIG. 4 oriented to establish the desired outwardly-diverging, air pattern or envelope directed generally toward the lower extremities of the patient 3 as schematically illustrated in FIGS. 1 and 2. The air envelope in this embodiment essentially surrounds the head of the patient and is substantially characterized by an air enclosure represented by boundary A in FIG. 4. During a dental operation involving drilling and utilizing the invention apparatus under controlled, experimental conditions, most of the particles, and all of the saliva splash, blood, aerosols were seen to move in many directions and to strike the inner boundary of the air stream and then to be carried downstream by the air to impact and collect on the disposable absorbent drape 10 resulting on the patient 3. Drape 10 effectively provides an absorbent bottom boundary or wall for the envelope of air. Of significant importance, it was noted that with the light remaining in a fixed position, the patient's head could be tilted to the right or left without loss of the desired protective air screen. The light position did not require readadjustment when the patient's head was tilted. Throughout the operation, the oral cavity 7 was, of course, totally visible to the dentist 1 and dental assistant 2. It was also found that the presence of the dentist's arms and hands penetrating the sides of the air shield did not substantially impair the effectiveness of the air stream with regard to foreign matter propelled from the oral cavity 7 of the patient. Some of such foreign matter did strike and cling to the gloved hands of the dentist 1 during the operation much of which would otherwise have reached the face and respiratory tract of either the dentist 1 or the dental assistant 2. Thus, a dramatic reduction in exposure to the normal grime was experienced and accordingly a substantial reduction in risk of being infected by the patient was also achieved.

It is contemplated that the pressure levels and thus the force of the air stream will be adjusted according to the nature of the operation, whether the patient is a child or adult, the contamination risk and like considerations. The invention recognize that the air light 8 of FIG. 1 and 2 may be designed to produce many different air enclosure shapes to meet particular needs to the procedure being done.

The invention contemplates the need for a retrofit assembly to quickly and easily provide a dental or medical operating light not so equipped with apparatus capable of producing the desired protective air enclosure or envelope.

Figure 3:
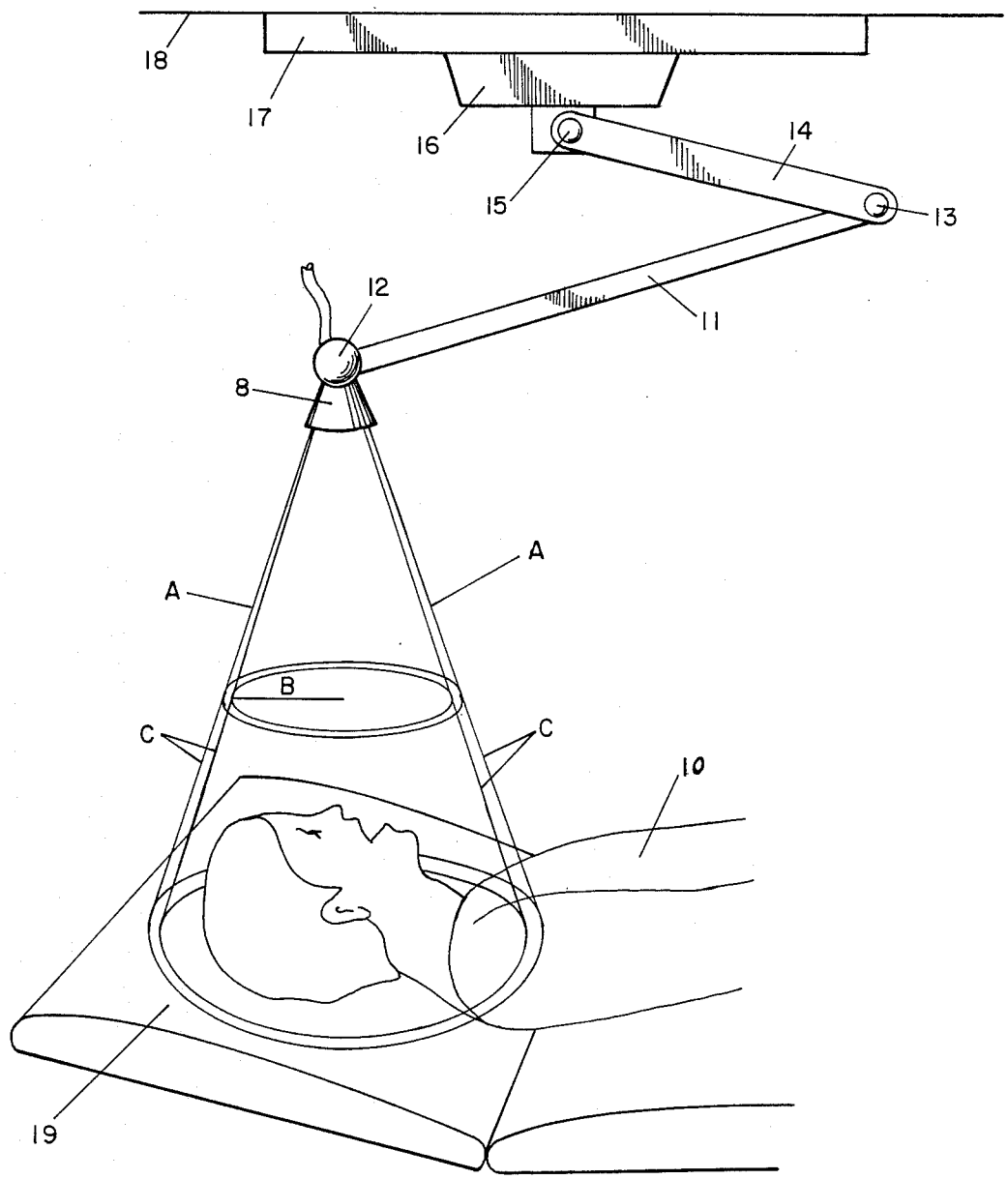
FIG. 3 is a somewhat schematic view of the light illustrated in the embodiment of FIG. 2 and the pattern of the air stream emerging therefrom.

Another embodiment of the present invention is illustrated somewhat schematically in FIGS. 3 and 4, and in this embodiment the mounting for the air light 8 is not directly connected to a dental chair and it permits a wide range of movement. More specifically, the air light 8 is carried at the extending end of a conventional linkage consisting of a first element 11 connected at one end thereof to the air light 8 through a universal connection joint 12 that permits a wide range of movement of the air light 8 and connected at its other end through a pivotal connection 13, to a second linkage element 14. The second linkage element 14, in turn, is pivotally connected to a rotatable turret member 15 that is fixed to a carriage 16 mounted for sliding movement along a track 17 supported at surface 18 which may be ceiling surface or an overhead support. By virtue of this mounting arrangement it will be apparant that the air light 8 may be positioned at a wide variety of locations and dispositions to emit an air enclosure from almost any desired position toward the surface (e.g. headrest) 19 on which the patient is supported, and the various joints in the linkage system can be designed in a conventional manner to permit such positioning of the air light 8 with relative ease while maintaining air light 8 in place after it is moved to its desired position. Compressed air can be supplied to the air light 8 from a convenient source of compressed air, such as that described above, and the air may be carried to the air light 8 in any convenient manner, such as through flexible tubing which readily permits the wide range of positioning movement of the air light 8 as described above.

As best seen in FIG. 4 the air light 8 is provided with orifices 9 the number, form and location of which can be selected to provide the desired envelope of air that is to be directed toward the patient to essentially surround the patient's head on the surface 19 to permit side-to-side movement, or other limited movement, of the patient's head without substantially disrupting the air flow envelope. Thus, the orifices 9 may be designed to create a generally circular air flow pattern having a radius B and having a thickness A, both of which may gradually increase as the air stream moves away from the nozzle, and as illustrated in FIGS. 3 and 4. With this arrangement, and the wide range of movement of the air light 8 as described above, it will be appreciated that the dental or medical team can selectively vary the effective size of the protective air envelope by varying the position of the air light 8 with respect to the surface 19 on which the patient is supported. For example, as shown in FIG. 3 in dotted lines, the effective diameter of the air envelope could be reduced by decreasing the distance between air light 8 and surface 19.

Thus, in the embodiment illustrated in FIGS. 3 and 4, the protective advantages described above resulting from an air flow envelope surrounding a patient's head are obtained, and an added flexibility is provided by virtue of the wide range of movement permitted for the air light 8 which can be useful in some applications. For example, in addition to utilizing the air light 8 for creating a protective air envelope at the headrest of a dental chair, the air light 8 could be used in conjunction with the surface of an operating table where the patient receives surgical treatment from a medical team, and where the surgery may result in high blood loss or other complications that may necessitate the presence of a protective air envelope.

In summary, at least the following advantages are obtained:

(1) Whether the patient's head is erect or tilted to one side or the other, the dental team is assured of adequate protection from projected particles irrespective of direction.

(2) The dental or medical operation proceeds in a normal manner without restriction of the work area.

(3) Since the air light 8 air source is offset from the oral cavity and face of the patient there is no impairment of vision and no impairment of routine operative motions.

(4) No adjustment of the nozzle or its position is required when the patient's head is tilted or is erect after being tilted.

(5) The patient is essentially unaware of the protective air screen with minimal or no air-skin or turbulent air-nose contact and is not required to support the nozzle or associated apparatus.

(6) When a nitrous oxide mask is employed, air light 8 and consequently the defined air stream can be positioned above the mask and above the area in which the dentist's hands operate and residual nitrous oxide can be disbursed.

(7) Substantial variation in the form and velocity of the air envelope is available to meet specific patient conditions, facial disfigurement, child treatments, and the like.

(8) Sterilization of the nozzle and associated hardware is facilitated by a quick connect-disconnect structure.

(9) The dental or medical team receives a cooling effect, an input of air fragrance and has reduced exposure to odors during treatment.

(10) Eye damage caused by foreign matter propelled from the oral cavity of the patient toward the operator has been substantially eliminated.

(11) Most importantly, risk of exposure to lethal pathogens and potential respiratory and skin infection from the patient is eliminated or at least substantially reduced.

(12) The patient is likewise protected from infectious transmission from the dental or medical team.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. For example it is recognized that any number of quick disconnect nozzles could be incorporated with the light to modified air patterns as may be required in various medical and dental procedures.

The foregoing disclosure is not intended or to be construed to limit the present invention or otherwise to exclude any such other embodiments, adaptations, variations, modifications and equivalent arrangements, the present invention being limited only by the columns appended hereto and the equivalents thereof.

What is claimed is:

1. A system for providing an air screen barrier to protect a dental team working on a patient positioned in a dental chair, said system comprising:
   (a) a source of pressurized air,
   (b) a nozzle connected to said pressurized air,
   (c) said nozzle including a plurality of air holes whereby the pressurized air is emitted in a continuous air flow pattern,
   (d) means for positioning said nozzle in a desired position with respect to the patient's head, whereby said continuous air flow pattern forms a protective air flow envelop about the patient's head.

2. The apparatus of claim 1 wherein a light is associated with the nozzle such that illumination is provided about the protective air flow area.

3. A method of providing protection to dental teams working on a patient positioned in a dental chair, said method comprising the steps of:
   (a) providing a source of pressurized air,
   (b) connecting said source of pressurized air to a nozzle which provides a continuous air flow pattern that forms a protective air envelope,
   (c) positioning said nozzle in a manner so as to provide a continuous protective air envelope about the patient's head.

* * * * *